(12) United States Patent
Legrand

(10) Patent No.: US 7,442,214 B2
(45) Date of Patent: Oct. 28, 2008

(54) DYE COMPOSITION COMPRISING AT LEAST ONE NON-IONIC ASSOCIATIVE POLYMER AND PROCESS FOR DYEING KERATIN FIBERS USING SAME

(75) Inventor: Frédéric Legrand, Tokyo (JP)

(73) Assignee: L'Oreal S.A., Paris (FR)

( * ) Notice: Subject to any disclaimer, the term of this patent is extended or adjusted under 35 U.S.C. 154(b) by 191 days.

(21) Appl. No.: 11/393,696

(22) Filed: Mar. 31, 2006

(65) Prior Publication Data

US 2006/0265817 A1 Nov. 30, 2006

Related U.S. Application Data

(60) Provisional application No. 60/681,150, filed on May 16, 2005.

(30) Foreign Application Priority Data

Mar. 31, 2005 (FR) ................................. 05 50841

(51) Int. Cl.
*A61Q 5/10* (2006.01)
(52) U.S. Cl. ...................... 8/405; 8/406; 8/407; 8/435; 8/552; 8/554; 8/559; 8/580; 8/582
(58) Field of Classification Search ................... 8/405, 8/406, 407, 435, 552, 554, 559, 580, 582
See application file for complete search history.

(56) References Cited

U.S. PATENT DOCUMENTS

| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,961,347 A | 11/1960 | Floyd |
| 3,206,462 A | 9/1965 | McCarty |
| 3,227,615 A | 1/1966 | Korden |
| 3,472,840 A | 10/1969 | Stone et al. |
| 3,632,559 A | 1/1972 | Basel et al. |
| 3,836,537 A | 9/1974 | Boerwinkle et al. |
| 3,874,870 A | 4/1975 | Green et al. |
| 3,912,808 A | 10/1975 | Sokol |
| 3,917,817 A | 11/1975 | Vanlerberghe et al. |
| 3,929,990 A | 12/1975 | Green et al. |
| 3,966,904 A | 6/1976 | Green et al. |
| 3,986,825 A | 10/1976 | Sokol |
| 4,001,432 A | 1/1977 | Green et al. |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,031,307 A | 6/1977 | DeMartino et al. |
| 4,131,576 A | 12/1978 | Iovine et al. |
| 4,157,388 A | 6/1979 | Christiansen |
| 4,165,367 A | 8/1979 | Chakrabarti |
| 4,172,887 A | 10/1979 | Vanlerberghe et al. |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,223,009 A | 9/1980 | Chakrabarti |
| 4,240,450 A | 12/1980 | Grollier et al. |
| 4,349,532 A | 9/1982 | Vanlerberghe et al. |
| 4,381,919 A | 5/1983 | Jacquet et al. |
| 4,422,853 A | 12/1983 | Jacquet et al. |
| 4,445,521 A | 5/1984 | Grollier et al. |
| 4,591,610 A | 5/1986 | Grollier |
| 4,608,250 A | 8/1986 | Jacquet et al. |
| 4,702,906 A | 10/1987 | Jacquet et al. |
| 4,719,099 A | 1/1988 | Grollier et al. |
| 4,719,282 A | 1/1988 | Nadolsky et al. |
| 4,761,273 A | 8/1988 | Grollier et al. |
| 4,839,166 A | 6/1989 | Grollier et al. |
| 4,948,579 A | 8/1990 | Jacquet et al. |
| 4,996,059 A | 2/1991 | Grollier et al. |
| 5,009,880 A | 4/1991 | Grollier et al. |
| 5,089,252 A | 2/1992 | Grollier et al. |
| 5,139,037 A | 8/1992 | Grollier et al. |
| 5,196,189 A | 3/1993 | Jacquet et al. |
| 5,480,459 A | 1/1996 | Mager et al. |
| 5,708,151 A | 1/1998 | Möckli |
| 5,792,221 A | 8/1998 | Lagrange et al. |
| 6,436,151 B2 * | 8/2002 | Cottard et al. .................. 8/406 |
| 6,800,098 B1 | 10/2004 | Allard et al. |
| 6,824,570 B2 | 11/2004 | Vidal et al. |

(Continued)

FOREIGN PATENT DOCUMENTS

DE 30 30 119 C2 2/1982

(Continued)

OTHER PUBLICATIONS

French Search Report for FR 0550841, dated Feb. 14, 2006.

(Continued)

*Primary Examiner*—Eisa B Elhilo
(74) *Attorney, Agent, or Firm*—Finnegan, Henderson, Farabow, Garrett & Dunner LLP

(57) ABSTRACT

The present disclosure relates to a dye composition comprising at least one dye, at least one fatty alcohol, at least one fatty acid ester, at least one surfactant chosen from non-ionic surfactants and anionic surfactants and at least one non-ionic associative polymer, wherein water is present in the dye composition in an amount greater than or equal to 55% by weight. The present disclosure further relates to a process for dyeing keratin fibers, including human keratin fibers, using such a composition and also to a multi-compartment kit separately comprising the dye composition and an oxidizing composition.

26 Claims, No Drawings

U.S. PATENT DOCUMENTS

| | | | |
|---|---|---|---|
| 6,881,230 | B2 | 4/2005 | Vidal |
| 6,884,265 | B2 | 4/2005 | Vidal et al. |
| 6,884,267 | B2 | 4/2005 | Vidal et al. |
| 6,893,471 | B2 | 5/2005 | Vidal |
| 7,001,436 | B2 | 2/2006 | Vidal et al. |
| 7,022,143 | B2 | 4/2006 | Vidal et al. |
| 7,060,110 | B2 | 6/2006 | Vidal et al. |
| 7,077,873 | B2 | 7/2006 | David et al. |
| 7,261,743 | B2 | 8/2007 | Plos et al. |
| 2001/0023514 | A1 | 9/2001 | Cottard et al. |
| 2003/0084516 | A9 | 5/2003 | Kravtchenko et al. |
| 2003/0106169 | A1 | 6/2003 | Vidal et al. |
| 2004/0093675 | A1 | 5/2004 | Vidal et al. |
| 2004/0093676 | A1 | 5/2004 | Vidal et al. |
| 2004/0098815 | A1 | 5/2004 | Schmenger et al. |
| 2004/0107513 | A1 | 6/2004 | Vidal et al. |
| 2004/0127692 | A1 | 7/2004 | David et al. |
| 2004/0143911 | A1 | 7/2004 | Vidal |
| 2004/0168263 | A1 | 9/2004 | Vidal |
| 2004/0187225 | A1 | 9/2004 | Vidal et al. |
| 2004/0200009 | A1 | 10/2004 | Vidal |
| 2004/0244123 | A1 | 12/2004 | Vidal et al. |
| 2005/0039268 | A1 | 2/2005 | Plos et al. |

FOREIGN PATENT DOCUMENTS

| | | |
|---|---|---|
| DE | 38 34 142 A1 | 4/1990 |
| EP | 0 080 976 B1 | 6/1983 |
| EP | 0 122 324 A1 | 10/1984 |
| EP | 0 337 354 A1 | 10/1989 |
| EP | 0 714 954 A2 | 6/1996 |
| FR | 1 400 366 | 4/1965 |
| FR | 1 492 597 | 7/1967 |
| FR | 1 583 363 | 10/1969 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 393 660 | 10/1978 |
| FR | 2 393 573 | 1/1979 |
| FR | 2 413 907 | 8/1979 |
| FR | 2 470 596 | 6/1981 |
| FR | 2 505 348 | 11/1982 |
| FR | 2 519 863 | 7/1983 |
| FR | 2 542 997 A1 | 9/1984 |
| FR | 2 598 611 A1 | 11/1987 |
| FR | 2 692 572 A1 | 12/1993 |
| FR | 2 803 195 A1 | 7/2001 |
| FR | 2 807 650 A1 | 10/2001 |
| FR | 2 822 693 A1 | 10/2002 |
| FR | 2 822 694 A1 | 10/2002 |
| FR | 2 822 696 A1 | 10/2002 |
| FR | 2 822 698 A1 | 10/2002 |
| FR | 2 825 625 A1 | 12/2002 |
| FR | 2 825 702 A1 | 12/2002 |
| FR | 2 829 926 A1 | 3/2003 |
| FR | 2 844 269 A1 | 3/2004 |
| GB | 1 021 400 | 3/1966 |
| GB | 1 331 819 | 9/1973 |
| GB | 1 347 051 | 2/1974 |
| GB | 1 479 786 | 7/1977 |
| GB | 1 546 809 | 5/1979 |
| WO | WO 95/01772 | 1/1995 |
| WO | WO 95/15144 | 6/1995 |
| WO | WO 02/078660 A1 | 10/2002 |
| WO | WO 02/100369 A2 | 12/2002 |
| WO | WO 02/100834 A1 | 12/2002 |

OTHER PUBLICATIONS

G. Fonnum et al., "Associative thickeners. Part I: Synthesis, rheology and aggregation behavior," Colloid & Polymer Science, No. 271, pp. 380-389 (1993).

English language abstract of DE 30 30 119 C2, Feb. 25, 1982.

English language abstract of DE 38 34 142 A1, Apr. 12, 1990.

English language abstract of EP 0 080 976 B1, Jun. 8, 1983.

* cited by examiner

DYE COMPOSITION COMPRISING AT LEAST ONE NON-IONIC ASSOCIATIVE POLYMER AND PROCESS FOR DYEING KERATIN FIBERS USING SAME

CROSS-REFERENCE TO RELATED APPLICATIONS

This application claims benefit of U.S. Provisional Application No. 60/681,150, filed May 16, 2005, the contents of which are incorporated herein by reference. This application also claims benefit of priority under 35 U.S.C. § 119 to French Patent Application No. FR 05 50841, filed Mar. 31, 2005, the contents of which are also incorporated herein by reference.

FIELD OF THE INVENTION

The present disclosure relates to a dye composition comprising at least one dye, at least one fatty alcohol, at least one fatty acid ester, at least one surfactant chosen from non-ionic surfactants and anionic surfactants, and at least one non-ionic associative polymer; the water content in the dye composition being greater than or equal to 55% by weight.

The present disclosure also relates, similarly, to a process for dyeing keratin fibers, including human keratin fibers, using such a composition, and also to a multi-compartment device comprising, at least one first compartment containing the dye composition and, at least one second compartment containing an oxidizing composition.

There exist essentially two methods of dyeing of keratin fibers, including human keratin fibers, such as the hair.

The first, called oxidation dyeing, or alternatively permanent dyeing, involves using oxidation dye precursors, which are colorless or relatively colorless substances. When they are placed in the presence of an oxidizing agent, these compounds produce, by means of a process of oxidative condensation that takes place actually inside the fiber, colored substances which remain trapped in the fiber.

The second, called direct dyeing, or alternatively semi-permanent dyeing, is obtained by using colored and coloring compounds that have an affinity for the keratin fibers to which they are applied. This type of dyeing does not require the use of an oxidizing agent to reveal the color, although it is not out of the question for this type of agent to be present during the process. In the latter case, reference is then made to lightening direct dyeing.

BACKGROUND OF THE INVENTION

The dye compositions of the prior art are, in the majority of cases, in the form of liquids, gels or creams which can be, if necessary, mixed, before application to the fibers, with an oxidizing composition.

The dye compositions are most commonly relatively rich in starting materials, among which are usually found fatty substances, surfactants and/or polymers. These compositions can be formulated such that they exhibit spreading properties and textures that can be readily handled so as to allow easy and rapid application to the fibers, while at the same time being sufficiently thick so as not to run beyond the areas intended to be dyed. Furthermore, these compositions should remain stable for the period of time they are left applied to the fibers, and it should be possible for them to be readily removed by rinsing once the coloration has been obtained.

Now, it is not uncommon to note that large amounts of starting materials can be detrimental to the dyeing effectiveness of such compositions. Less favorable kinetics, a reduced intensity of the shade obtained, poor color homogeneity from one fiber to the other and/or according to the site on the fiber (root/tip), etc., may thus be observed.

BRIEF DESCRIPTION OF THE INVENTION

There is, therefore, a need in the art to provide dye compositions which do not have at least one of the drawbacks mentioned above of the current dye compositions, while at the same time conserving the desired properties mentioned above.

Such a need can be fulfilled by means of the present disclosure, which relates to dye compositions comprising, in a medium suitable for dyeing keratin fibers:
- at least one fatty alcohol;
- at least one fatty acid ester of a $C_1$-$C_{10}$ alcohol;
- at least one surfactant chosen from non-ionic surfactants and anionic surfactants; and
- at least one non-ionic associative polymer;
- wherein said dye composition comprises water in an amount of greater than or equal to 55%.

The present disclosure also relates to a process for dyeing keratin fibers using such a composition, and where appropriate in the presence of an oxidizing composition.

Finally, the present disclosure relates to a device or multi-compartment kit comprising at least one first compartment containing a dye composition according to the disclosure and comprising at least one second compartment containing an oxidizing composition.

The composition according to the disclosure can result in less degradation of the coloration properties and can make it possible to obtain colorations that are stronger, more homogeneous and more chromatic, while at the same time conferring good cosmetic properties on the fibers treated and limiting the degradation thereof.

The compositions in accordance with the present disclosure can exhibit, moreover, an ideal texture for use in the dyeing of human keratin fibers, including the hair. They are in fact creamy, and can be sufficiently thick for rapid and easy application, with good removal by rinsing, without however running beyond the areas of the head of hair intended to be treated.

Other characteristics and benefits of the disclosure will emerge more clearly upon reading the description and the examples below.

According to the present disclosure, and unless otherwise indicated, it is specified that the limits of value ranges are included in these ranges.

Also according to the present disclosure, when mention is made of a compound comprising a fatty chain, this chain can be a saturated or unsaturated, linear or branched hydrocarbon-based chain comprising from 8 to 30 carbon atoms, such as from 10 to 24 carbon atoms.

As used herein, the expression "at least one" is understood to mean one or more individual compounds, and also mixtures thereof.

As discussed above, the present disclosure is suitable for the dyeing of keratin fibers, including human keratin fibers, such as, for instance, the hair.

As has been indicated above, the dye composition according to the disclosure has a water content greater than or equal to 55% by weight, relative to the weight of said dye composition.

In accordance with one embodiment of the present disclosure, for example, the water content is greater than or equal to 60% by weight, relative to the weight of said dye composition.

The composition comprises, moreover, at least one fatty alcohol. This fatty alcohol is non-oxyalkylenated and non-glycerolated. By way of non-limiting example, the fatty alcohol can be chosen from $C_8$-$C_{30}$, for instance $C_{10}$-$C_{24}$, such as $C_{12-24}$, saturated and unsaturated, linear and branched alcohols optionally comprising at least one other hydroxyl group. By way of further examples, non-limiting mention may be made, inter alia, of oleyl alcohol, lauryl alcohol, palmityl alcohol, myristyl alcohol, behenyl alcohol, stearyl alcohol, linoleyl alcohol, linolenyl alcohol, capryl alcohol, arachidonyl alcohol, and mixtures thereof.

According to another embodiment of the present disclosure, for instance, the total amount of fatty alcohols present in the composition can range from 0.1% to 30% by weight, relative to the total weight of the dye composition. For example, the total content of fatty alcohols present can range from 0.5% to 20% by weight, relative to the weight of the dye composition.

For further example, in still another embodiment, the composition according to the disclosure can comprise at least one other fatty substance different from the abovementioned fatty alcohols. Thus, the composition can further comprise, as a fatty substance, at least one compound chosen from non-oxyalkylenated, nonglycerolated fatty acid amides, mineral oils and plant oils.

The fatty acid amides can be chosen from, for instance, compounds derived from an alkanolamine and from a $C_8$-$C_{30}$ fatty acid. They can be, for example, chosen from amides of a $C_2$-$C_{10}$ alkanolamine and of a $C_{14}$-$C_{30}$ fatty acid, such as from amides of a $C_2$-$C_{10}$ alkanolamine and of a $C_{14}$-$C_{22}$ fatty acid.

In one embodiment, for example, the fatty acid amide can be chosen from:
  oleic acid diethanolamide, such as the amide sold under the trade name Mexanyl® GT by the company Chimex,
  myristic acid monoethanolamide, such as the amide sold under the trade name Comperlan® MM by the company Cognis,
  soy bean fatty acid diethanolamide, such as the amide sold under the trade name Comperlan® VOD by the company Cognis,
  stearic acid ethanolamide, such as the amide sold under the trade name Monamid® S by the company Uniqema,
  oleic acid monoisopropanolamide, such as the amide sold under the trade name Witcamide® 61 by the company Witco,
  linoleic acid diethanolamide, such as the amide sold under the trade name Purton® SFD by the company Zschimmer Schwarz,
  stearic acid monoethanolamide, such as the amide sold under the trade name Monamid® 972 by the company ICI/Uniqema,
  behenic acid monoethanolamide, such as the amide sold under the trade name Incromide® BEM from Croda,
  isostearic acid monoisopropanolamide, such as the amide sold under the trade name Witcamide® SPA by the company Witco,
  erucic acid diethanolamide, such as the amide sold under the trade name erucic acid diethanolamide by the company Stearineries Dubois, and
  ricinoleic acid monoethanolamide, such as the amide sold under the trade name ricinoleic monoethanolamide by the company Stearineries Dubois.

Liquid paraffin is a non-limiting example of a mineral oil that may be used as a fatty substance in the composition.

As regards the plant oils, non-limiting mention may be made of, for example, avocado oil, olive oil or liquid jojoba wax.

According to one embodiment of the disclosure, the total amount of fatty substances, other than the abovementioned fatty alcohols, can be present in an amount ranging from 0.1% to 30% by weight of the dye composition. For instance, the total amount of fatty substances other than the abovementioned fatty alcohols, can be present in an amount ranging from 0.5% to 20% by weight, relative to the weight of the dye composition.

The composition according to the composition comprises, moreover, at least one fatty acid ester of a $C_1$-$C_{10}$ alcohol.

For instance, said ester can be chosen from monoesters, diesters, and triesters of linear and branched, saturated and unsaturated $C_8$-$C_{30}$ carboxylic acids, and of linear and branched, saturated and unsaturated $C_1$-$C_{10}$ monohydroxylated and polyhydroxylated alcohols.

In one embodiment, for example, the ester can be chosen from monoesters, diesters and triesters of oleic acid, lauric acid, palmitic acid, myristic acid, behenic acid, stearic acid, linoleic acid, linolenic acid, capric acid or arachidonic acid, and of methanol, ethanol, propanol, isopropanol, ethylene glycol, glycerol, octanol and decanol.

According to another embodiment of the present disclosure, the at least one fatty acid ester of a $C_1$-$C_{10}$ alcohol can be present in an amount ranging from 0.1% to 30% by weight, relative to the weight of the dye composition. For instance, the at least one fatty acid ester of a $C_1$-$C_{10}$ alcohol can be present in an amount ranging from 0.5% to 20% by weight, relative to the weight of the dye composition. According to yet another embodiment, the at least one fatty acid ester of a $C_1$-$C_{10}$ alcohol can be present in an amount ranging from 1% to 15% by weight, relative to the weight of the dye composition.

The composition according to the disclosure comprises, moreover, at least one surfactant chosen from non-ionic surfactants and anionic surfactants.

Among the non-ionic surfactants, non-limiting mention may be made of those chosen from alkoxylated and/or glycerolated non-ionic surfactants.

By way of further non-limiting example, the non-ionic surfactants can be chosen from:
  oxyalkylenated or glycerolated fatty alcohols;
  oxyalkylenated alkylphenols in which the alkyl chain is of $C_8$-$C_{18}$;
  oxyalkylenated or glycerolated fatty amides;
  oxyalkylenated plant oils;
  optionally oxyalkylenated $C_6$-$C_{30}$ acid esters of sorbitan;
  optionally oxyalkylenated fatty acid esters of sucrose;
  fatty acid esters of polyethylene glycol;
  ($C_6$-$C_{30}$)alkyl polyglycosides;
  N-($C_6$-$C_{30}$)alkylglucamine derivatives;
  amine oxides such as ($C_{10}$-$C_{14}$)alkylamine oxides or N-acylaminopropylmorpholine oxides;
  copolymers of ethylene oxide and of propylene oxide; and mixtures thereof.

In one embodiment, for example, the mean number of oxyalkylenated units can range from 2 to 150 units. In another embodiment, they may be chosen from oxyethylenated and/or oxypropylenated units.

With respect to the glycerolated surfactants, they can comprise, for example, from 1 to 20, such as from 1.5 to 5, glycerol groups.

In accordance with another embodiment of the disclosure, the non-ionic surfactants may be chosen from oxyalkylenated or glycerolated fatty alcohols.

Among the anionic surfactants, non-limiting mention may be made of:

- ($C_6$-$C_{30}$)alkyl sulphates, ($C_6$-$C_{30}$)alkyl ether sulphates, ($C_6$-$C_{30}$)alkylamido ether sulphates, alkylaryl polyether sulphates, monoglyceride sulphates;
- ($C_6$-$C_{30}$)alkyl sulphonates, ($C_6$-$C_{30}$)alkylamide sulphonates, ($C_6$-$C_{30}$)alkylaryl sulphonates, α-olefin sulphonates, paraffin sulphonates;
- ($C_6$-$C_{30}$)alkyl phosphates;
- ($C_6$-$C_{30}$)alkyl sulphosuccinates, ($C_6$-$C_{30}$)alkyl ether sulphosuccinates, ($C_6$-$C_{30}$)alkylamide sulphosuccinates;
- ($C_6$-$C_{30}$)alkyl sulphoacetates;
- ($C_6$-$C_{24}$)acyl sarcosinates;
- ($C_6$-$C_{24}$)acyl glutamates;
- ($C_6$-$C_{30}$)alkylpolyglycoside carboxylic ethers;
- ($C_6$-$C_{30}$)alkylpolyglycoside sulphosuccinates;
- ($C_6$-$C_{30}$)alkyl sulphosuccinamates;
- ($C_6$-$C_{24}$)acyl isethionates;
- N-($C_6$-$C_{24}$)acyl taurates;
- fatty acid salts;
- ($C_8$-$C_{20}$)acyl lactylates;
- ($C_6$-$C_{30}$)alkyl-D-galactoside uronic acid salts;
- polyoxyalkylenated ($C_6$-$C_{30}$)alkyl ether carboxylic acid salts, polyoxyalkylenated ($C_6$-$C_{30}$)alkylaryl ether carboxylic acid salts, polyoxyalkylenated ($C_6$-$C_{30}$)alkylamido ether carboxylic acid salts;
- and mixtures thereof.

These anionic surfactants can also be in the form of salts in the composition according to the disclosure, such as salts of alkali metals, for instance sodium; of alkaline-earth metals, for instance magnesium; ammonium salts; amine salts; amino alcohol salts. Depending on the conditions, they may also be in the acid form thereof.

It should be noted that the alkyl or acyl radicals of these various compounds may contain, for example, from 12 to 20 carbon atoms. In one embodiment, the aryl radical may be chosen from phenyl and benzyl groups.

Furthermore, the polyoxyalkylenated anionic surfactants may comprise, for instance, from 2 to 50 alkylene oxide, such as ethylene oxide, groups.

The at least one surfactant chosen from non-ionic surfactants and anionic surfactants can be present, for example, in an amount ranging from 0.1% to 40% by weight, relative to the weight of the dye composition, for instance, from 0.5% to 30% by weight, relative to the weight of the dye composition, such as from 1% to 20% by weight, relative to the weight of the dye composition.

The composition comprises, moreover, at least one non-ionic associative polymer.

By way of non-limiting example, the associative polymers can be chosen from:

(1) celluloses modified with groups comprising at least one fatty chain; among which mention may be made, by way of non-limiting examples, of:
hydroxyethylcelluloses modified with groups comprising at least one fatty chain, such as alkyl, arylalkyl or alkylaryl groups, or mixtures thereof, and in which the alkyl groups can be, for example, $C_8$-$C_{22}$, such as the product Natrosol Plus Grade 330 CS® ($C_{16}$ alkyls) sold by the company Aqualon, or the product Bermocoll EHM 100® sold by the company Berol Nobel,
those modified with alkylphenyl polyalkylene glycol ether groups, such as the product Amercell Polymer HM-1500® (nonylphenol polyethylene glycol (15) ether) sold by the company Amerchol.

(2) hydroxypropyl guars modified with groups comprising at least one fatty chain, such as, for example, the product Esaflor HM 22® ($C_{22}$ alkyl chain) sold by the company Lamberti, or the products RE210-18® ($C_{14}$ alkyl chain) and RE205-1® ($C_{20}$ alkyl chain) sold by the company Rhone Poulenc;

(3) copolymers of vinylpyrrolidone and of hydrophobic monomers comprising a fatty chain, for which mention may be made, by way of non-limiting examples, of:
the products Antaron V216® or Ganex V216® (vinylpyrrolidone/hexadecene copolymer) sold by the company I.S.P.;
the products Antaron V220® or Ganex V220® (vinylpyrrolidone/eicosene copolymer) sold by the company I.S.P.;

(4) copolymers of $C_1$-$C_6$ alkyl methacrylates or acrylates and of amphiphilic monomers comprising at least one fatty chain, such as, for example, the oxyethylenated methyl acryate/stearyl acrylate copolymer sold by the company Goldschmidt under the name Antil 208®;

(5) copolymers of hydrophilic methacrylates or acrylates and of hydrophobic monomers comprising at least one fatty chain, such as, for example, polyethylene glycol methacrylate/lauryl methacrylate copolymer;

(6) polyether polyurethanes comprising, in their chain, both hydrophilic blocks, most commonly polyoxyethylenated in nature, and hydrophobic blocks which may, for example, be aliphatic chains alone and/or cycloaliphatic and/or aromatic chains;

(7) polymers with an aminoplast-ether backbone having at least one fatty chain, such as the compounds Pure Thix® proposed by the company Sud-Chemie.

The polyether polyurethanes may comprise, for example, at least two hydrocarbon-based lipophilic chains having from 8 to 30 carbon atoms, separated by a hydrophilic block, it being possible for the hydrocarbon-based chains to be pendant chains or chains at the end of a hydrophilic block.

For instance, in one embodiment, it is possible for at least one pendant chain to be used.

In addition, the polymer may comprise a hydrocarbon-based chain at one end or at both ends of a hydrophilic block.

The polyether polyurethanes can be multiblock, such as in triblock form. The hydrophobic blocks may be at each end of the chain (for example: triblock copolymer with a hydrophilic central block) or can be distributed both at the ends and in the chain (multiblocked copolymer, for example). These same polymers can also be grafted polymers or star polymers.

The non-ionic polyether polyurethanes comprising a fatty chain may be triblock copolymers in which the hydrophilic block is a polyoxyethylenated chain comprising from 50 to 1000 oxyethylenated groups. The non-ionic polyether polyurethanes comprise a urethane bond between the hydrophilic blocks, hence the origin of the name.

By extension, also among the non-ionic polyether polyurethanes comprising a fatty chain are those in which the hydrophilic blocks are linked to the lipophilic blocks via other chemical bonds.

By way of examples of non-ionic polyether polyurethanes comprising a fatty chain that can be used in the present disclosure, non-limiting mention may also be made of Rheolate 205® comprising a urea functional group, sold by the company Rheox, or else Rheolate® 208, 204 or 212, and also Acrysol RM 184®.

Non-limiting mention may also be made of the product Elfacos T210® comprising a $C_{12}$-$C_{14}$ alkyl chain and the product Elfacos T212® comprising a $C_{18}$ alkyl chain, from Akzo.

The product DW 1206B® from Rohm & Haas, comprising a $C_{20}$ alkyl chain and a urethane bond, provided with a 20% solids content in water, can also be used.

Use may also be made of solutions or dispersions of these polymers, for instance in water or in an aqueous-alcoholic medium. By way of example of such polymers, non-limiting mention may be made of Rheolate® 255, Rheolate® 278 and Rheolate® 244, sold by the company Rheox. Use may also be made of the product DW 1206F and DW 1206J provided by the company Rohm & Haas.

The polyether polyurethanes that can be used according to the disclosure are described, for instance, in the article by G. Fonnum, J. Bakke and Fk. Hansen—Colloid Polym. Sci 271, 380.389 (1993).

In one embodiment, according to the present disclosure, use may be made of a polyether polyurethane which can be obtained by polycondensation of at least three compounds comprising (i) at least one polyethylene glycol comprising from 150 to 180 mol of ethylene oxide, (ii) stearyl alcohol or decyl alcohol and (iii) at least one diisocyanate. Such polyether polyurethanes are sold, for instance, by the company Rohm & Haas under the names Aculyn 46® and Aculyn 44®. Aculyn 46® is a polycondensate of polyethylene glycol comprising 150 or 180 mol of ethylene oxide, of stearyl alcohol and of methylenebis(4-cyclohexyl isocyanate) (SMDI), at 15% by weight in a matrix of maltodextrin (4%) and of water (81%); Aculyn 44® is a polycondensate of polyethylene glycol comprising 150 or 180 mol of ethylene oxide, decyl alcohol and methylenebis(4-cyclohexyl isocyanate) (SMDI), at 35% by weight in a mixture of propylene glycol (39%) and of water (26%).

The composition can comprise the at least one non-ionic associative polymer in an amount ranging from 0.01% to 5% by weight, relative to the weight of the dye composition. In one embodiment, for example, the at least one associative polymer is present in an amount ranging from 0.02% to 3% by weight, relative to the weight of the dye composition.

The composition according to the disclosure also comprises at least one dye chosen from oxidation dye precursors and direct dyes.

The at least one oxidation dye precursor can be chosen from oxidation bases and couplers.

The oxidation bases are chosen from the oxidation bases conventionally used for oxidation dyeing, among which non-limiting mention may be made of para-phenylenediamines, bisphenylalkylenediamines, para-aminophenols, ortho-aminophenols and heterocyclic bases and addition salts thereof with an acid or with an alkaline agent.

Among the para-phenylenediamines, mention may be made, by way of example, of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine and 4'-aminophenyl-1-(3-hydroxy)pyrrolidine, and the addition salts thereof with an acid or with an alkaline agent.

Among the para-phenylenediamines mentioned above, mention may be made of para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid or with an alkaline agent.

Among the bis(phenyl)alkylenediamines, mention may be made, by way of example, of N,N'-bis(β-hydroxyethyl)-N, N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,5-dioxaoctane, and the addition salts thereof with an acid or with an alkaline agent.

Among the para-aminophenols, mention may be made, by way of example, of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid or with an alkaline agent.

Among the ortho-aminophenols, mention may be made, by way of example, of 2-aminophenol, 2-amino-5-methylphenol, 2-amino-6-methylphenol and 5-acetamido-2-aminophenol, and the addition salts thereof with an acid or with an alkaline agent.

Among the heterocyclic bases, mention may be made, by way of example, of pyridine derivatives, such as 2,3-diamino-6-methoxypyridine; pyrimidine derivatives, such as, for instance, 2,4,5,6-tetraaminopyrimidine or 4-hydroxy-2,5,6-triaminopyrimidine; and pyrazole derivatives, such as 1N-β-hydroxyethyl-4,5-diaminopyrazole; and the addition salts thereof with an acid or with an alkaline agent.

When used, the at least one oxidation base can be present in an amount, for example, from 0.0005% to 12% by weight, relative to the weight of the dye composition, such as from 0.005% to 6% by weight, relative to the weight of the dye composition.

The composition may also comprise, combined with at least one oxidation base, at least one coupler so as to modify or to enrich with tints the shades obtained.

The coupler(s) that may be used may be chosen from the couplers conventionally used in oxidation dyeing, and among which non-limiting mention may be made of meta-phenylenediamines, meta-aminophenols, meta-diphenols and heterocyclic couplers, and the addition salts thereof with an acid or with an alkaline agent.

For example, these couplers can be chosen from 2-methyl-5-aminophenol, 5-N-(β-hydroxyethyl)amino-2-methylphenol, 3-aminophenol, 2-methyl-5-amino-6-chlorophenol, 1,3-dihydroxybenzene, 1,3-dihydroxy-2-methylbenzene, 4-chloro-1,3-dihydroxybenzene, 2,4-diamino-1-β-hydroxyethyloxy)benzene, 2-amino-4-(β-hydroxylethylamino)-1- methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2-amino-3-hydroxypyridine, 2,6-dihydroxy-4-methylpyridine, 1H-3-methylpyrazol-5-one, 1-phenyl-3-methylpyrazole-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, and the addition salts thereof with an acid or with an alkaline agent.

When they are present, the coupler(s) can be present, for example, in an amount ranging from 0.0001% to 15% by weight, such as from 0.005% to 12% by weight, relative to the weight of the dye composition. In accordance with one embodiment, the at least one coupler is present in an amount ranging from 0.01% to 10% by weight, relative to the weight of the dye composition.

In general, for example, the addition salts with an acid can be chosen from hydrochlorides, hydrobromides, sulphates, citrates, succinates, tartrates, tosylates, benzenesulphonates, lactates and acetates.

The direct dye(s) can be, for example, chosen from those of non-ionic, cationic and anionic nature.

By way of non-limiting examples, mention may be made of nitrobenzene dyes, azo, azomethine, methine, tetraazapentamethine, anthraquinone, naphthoquinone, benzoquinone, phenothiazine, indigoid, xanthene, phenanthridine, phthalocyanin and triarylmethane-based dyes, and natural dyes, alone or as mixtures.

The direct dye(s), for example, may be chosen from the following red or orange nitrobenzene dyes:
1-hydroxy-3-nitro-4-N-(γ-(hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)benzene,
1-(β,γ-dihydroxypropyl)oxy-3-nitro-4-(β-hydroxyethyl)aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine, and
1-amino-2-nitro-4-hydroxy-5-methylbenzene.

The direct dye(s) may also be chosen from yellow and green-yellow nitrobenzene direct dyes; non-limiting mention may, for example, be made of the compounds chosen from:
1-β-hydroxyethyloxy-3-methylamino-4-nitrobenzene,
1-methylamino-2-nitro-5-(β,γ-dihydroxypropyl)oxybenzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulphonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene, and
4-(β-hydroxyethyl)amino-3-nitrobenzamide.

Non-limiting mention may also be made of blue or violet nitrobenzene direct dyes, for instance:
1-(β-hydroxyethyl)amino-4-N,N-bis(β-hydroxyethyl)amino-2-nitrobenzene,
1-(γ-hydroxypropyl)amino-4-N,N-bis(β-hydroxyethyl)amino-2-nitrobenzene,
1-(β-hydroxyethyl)amino-4-(N-methyl-N-β-hydroxyethyl)amino-2-nitrobenzene,
1-(β-hydroxyethyl)amino-4-(N-ethyl-N-β-hydroxyethyl)amino-2-nitrobenzene,
1-(β,γ-dihydroxypropyl)amino-4-(N-ethyl-N-β-hydroxyethyl)amino-2-nitrobenzene,
2-nitro-para-phenylenediamines having the following formula:

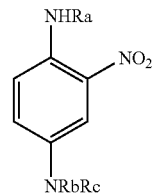

in which:
Rb is chosen from $C_1$-$C_4$ alkyl radicals, and β-hydroxyethyl, β-hydroxypropyl and γ-hydroxypropyl radicals;
Ra and Rc, which may be identical or different, are chosen from β-hydroxyethyl, β-hydroxypropyl, γ-hydroxypropyl and β,γ-dihydroxypropyl radicals, wherein at least one of the radicals Rb, Rc or Ra is a γ-hydroxypropyl radical and with the proviso that Ra and Rc are not simultaneously a β-hydroxyethyl radical when Rb is a γ-hydroxypropyl radical, such as those described in French Patent No. FR 2 692 572.

Among the azo direct dyes that may be used according to the disclosure, non-limiting mention may be made of the cationic azo dyes described in the documents WO 95/15144, WO 95/01772, EP 0 714 954, FR 2 822 696, FR 2 825 702, FR 2 825 625, FR 2 822 698, FR 2 822 693, FR 2 822 694, FR 2 829 926, FR 2 807 650, WO 02/078660, WO 02/100834, WO 02/100369 and FR 2 844 269.

Among these compounds, mention may be made of the following dyes:
1,3-dimethyl-2-[[4-(dimethylamino)phenyl]azo]-1Himidazolium chloride,
1,3-dimethyl-2-[(4-aminophenyl)azo]-1H-imidazolium chloride, and
1-methyl-4-[(methylphenylhydrazono)methyl]pyridinium methyl sulphate.

Among the azo direct dyes, further mention may also be made of the following dyes described in the Color Index International 3rd edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24 and Disperse Black 9.

Mention may also be made of 1-(4'-aminodiphenylazo)-2-methyl-4-[bis(β-hydroxyethyl)amino]benzene and 4-hydroxy-3-(2-methoxyphenylazo)-1-naphthalenesulphonic acid.

Among the quinone direct dyes, non-limiting mention may be made of the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds:

1-N-methylmorpholiniumpropylamino-4-hydroxyanthraquinone,
1-aminopropylamino-4-methylaminoanthraquinone,
1-aminopropylaminoanthraquinone,
5-β-hydroxyethyl-1,4-diaminoanthraquinone,
2-aminoethylaminoanthraquinone, and
1,4-bis(β,γ-dihydroxypropylamino)anthraquinone.

In one embodiment of the present disclosure, the at least one azine dye can be chosen from the following compounds: Basic Blue 17, Basic Red 2.

Among the cationic methine direct dyes, non-limiting mention may also be made of Basic Red 14, Basic Yellow 13 and Basic Yellow 29.

Among the triarylmethane dyes that may be used according to the disclosure, non-limiting mention may be made of the following compounds: Basic Green 1, Acid Blue 9, Basic Violet 3, Basic Violet 14, Basic Blue 7, Acid Violet 49, Basic Blue 26 and Acid Blue 7.

Among the indoamine dyes that may be used according to the disclosure, non-limiting mention may be made of the following compounds:

2-β-hydroxyethylamino-5-[bis(β-4'-hydroxyethyl)amino] anilino-1,4-benzoquinone;
2-β-hydroxyethylamino-5-(2'-methoxy-4'-amino)anilino-1,4-benzoquinone;
3-N (2'-chloro-4'-hydroxy)phenylacetylamino-6-methoxy-1,4-benzoquinoneimine;
3-N (3'-chloro-4'-methylamino)phenylureido-6-methyl-1,4-benzoquinoneimine; and
3-[4'-N-(ethylcarbamylmethyl)amino]phenylureido-6-methyl-1,4-benzoquinoneimine.

The composition may also comprise at least one natural direct dye, such as lawsone, juglone, alizarine, purpurine, carminic acid, kermesic acid, purpurogallin, protocatechaldehyde, indigo, isatine, curcumin, spinulosine and apigenidine. Use may also be made of extracts or decoctions containing these natural dyes, for instance henna-based cataplasms or extracts.

The at least one direct dye, when present, can be present in an amount ranging from 0.0005% to 15% by weight, relative to the weight of the dye composition, such as from 0.005% to 12% by weight, relative to the weight of the dye composition. According to one embodiment of the disclosure, the at least one direct dye can be present in an amount ranging from 0.01% to 5% by weight, relative to the weight of the dye composition.

The composition according to the disclosure may also comprise at least one basifying agent.

Among the basifying agents, non-limiting mention may, for example, be made of aqueous ammonia, alkali metal carbonates, $C_2$-$C_{10}$ alkanolamines such as monoethanolamine, diethanolamine and triethanolamine and also derivatives thereof, oxyethylenated and/or oxypropylenated hydroxyalkylamines and ethylenediamines, sodium hydroxide, potassium hydroxide, alkali metal or alkaline-earth metal silicates and the compounds of the formula:

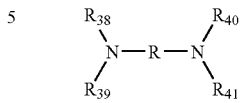

in which R is chosen from propylene residues optionally substituted with a hydroxyl group and $C_1$-$C_4$ alkyl radicals; $R_{38}$, $R_{39}$, $R_{40}$ and $R_{41}$, which may be identical or different, are chosen from hydrogen atoms, $C_1$-$C_4$ alkyl radicals, and $C_1$-$C_4$ hydroxyalkyl radicals.

In one embodiment, the at least one basifying agent is chosen from aqueous ammonia, alkanolamines and combinations of alkanolamines with alkali metal or alkaline-earth metal silicates.

According to another embodiment of the disclosure, the composition does not comprise aqueous ammonia as basifying agent.

It should, be noted, moreover, that the pH may also be adjusted by using acidifying agents, for instance mineral or organic acids such as hydrochloric acid, orthophosphoric acid or sulphuric acid, carboxylic acids, for instance acetic acid, tartaric acid, citric acid or lactic acid, or sulphonic acids.

The at least one basifying and/or acidifying agent may be present in such an amount that the pH of the dye composition ranges from 3 to 12, such as from 4 to 11, and for instance from 7 to 11.

The composition according to the disclosure may also comprise at least one cationic or amphoteric substantive polymers.

For the purposes of the present disclosure, the term "cationic polymer" is understood to mean any polymer containing cationic groups and/or groups that may be ionized into cationic groups. Such polymers can be chosen from those already known per se to improve the cosmetic properties of the hair, i.e. such as those described in European Patent Application No. EP-A-337 354 and in French Patent Nos. FR-2 270 846, FR-2 383 660, FR-2 598 611, FR-2 470 596 and FR-2 519 863.

The cationic polymers that may be used, according to one embodiment, may be chosen from those containing units comprising primary, secondary, tertiary and/or quaternary amine groups, which may either form part of the main polymer chain or may be borne by a side substituent directly attached thereto.

The cationic polymers that may be used can have a number-average molecular mass ranging from 500 to $5 \times 10^6$, such as from $10^3$ to $3 \times 10^6$.

Among the cationic polymers, mention may be made, for example, of polymers of the polyamine, polyaminoamide and polyquaternary ammonium type. These are known products. They are described, for instance, in French Patents Nos. FR-2 505 348 and FR-2 542 997. Among said polymers, non-limiting mention may be made of:

(1) Homopolymers or copolymers derived from acrylic or methacrylic esters or amides and comprising at least one of the units chosen from those of formulae (I), (II), (Ill) and (IV):

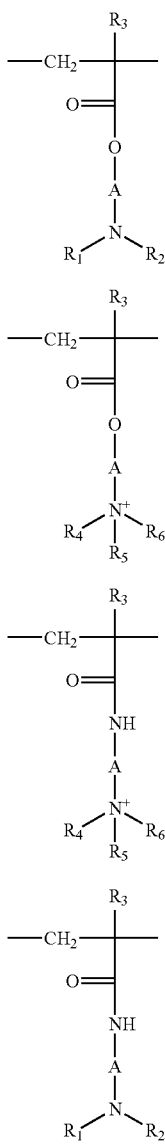

in which:

R$_3$, which may be identical or different, is chosen from hydrogen atoms and CH$_3$ radicals;

A, which may be identical or different, is chosen from linear and branched alkyl groups of 1 to 6 carbon atoms, such as 2 or 3 carbon atoms, and hydroxyalkyl groups of 1 to 4 carbon atoms;

R$_4$, R$_5$ and R$_6$, which may be identical or different, are chosen from alkyl groups having from 1 to 18 carbon atoms and benzyl radicals, such as an alkyl group having from 1 to 6 carbon atoms;

R$_1$ and R$_2$, which may be identical or different, are chosen from hydrogen atoms and alkyl groups having from 1 to 6 carbon atoms, such as methyl or ethyl;

X is an anion derived from an inorganic or organic acid, such as a methosulphate anion or a halide such as chloride or bromide.

The polymers of family (1) can also contain at least one unit derived from comonomers which may be chosen from the family of acrylamides, methacrylamides, diacetone acrylamides, acrylamides and methacrylamides substituted on the nitrogen with lower (C$_1$-C$_4$) alkyls, acrylic or methacrylic acids or esters thereof, vinyllactams such as vinylpyrrolidone or vinylcaprolactam, and vinyl esters.

Thus, among these polymers of family (1), non-limiting mention may be made of:

copolymers of acrylamide and of dimethylaminoethyl methacrylate quaternized with dimethyl sulphate or with a dimethyl halide, such as the product sold under the name Hercofloc by the company Hercules, copolymers of acrylamide and of methacryloyloxyethyltrimethyl ammonium chloride described, for example, in European Patent Application No. EP-A-080 976 and sold under the name Bina Quat P 100 by the company Ciba Geigy, copolymer of acrylamide and of methacryloyloxyethyltrimethyl ammonium methosulphate sold under the name Reten by the company Hercules, quaternized or non-quaternized vinylpyrrolidone/dialkylaminoalkyl acrylate or methacrylate copolymers, such as the products sold under the name "Gafquat" by the company ISP, for instance "Gafquat 734" or "Gafquat 755," or alternatively the products known as "Copolymer 845, 958 and 937." These polymers are described in detail in French Patent Nos. FR-2 077 143 and FR-2 393 573, dimethylaminoethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers sold for instance under the name Styleze CC 10 by ISP, and quaternized vinylpyrrolidone/dimethylaminopropyl methacrylamide copolymers such as the product sold under the name "Gafquat HS 100" by the company ISP.

(2) The cellulose ether derivatives comprising quaternary ammonium groups, which are described in French Patent No. FR-1 492 597, and for example the polymers sold under the names "JR" (JR 400, JR 125, JR 30M) or "LR" (LR 400, LR 30M) by the company Union Carbide Corporation. These polymers are also defined in the CTFA dictionary as hydroxyethylcellulose quaternary ammoniums that have reacted with an epoxide substituted with a trimethylammonium group.

(3) Cationic cellulose derivatives such as the copolymers of cellulose or cellulose derivatives grafted with a water-soluble quaternary ammonium monomer, described for instance, in U.S. Pat. No. 4,131,576, such as hydroxyalkylcelluloses, for instance hydroxymethyl-, hydroxyethyl- or hydroxypropylcelluloses grafted for example, with a methacryloylethyltrimethylammonium, methacrylamidopropyltrimethylammonium or dimethyldiallylammonium salt.

The commercial products corresponding to this definition include, for example, the products sold under the name Celquat L 200 and Celquat H 100 by the company National Starch.

(4) The cationic guar gums described for instance in U.S. Pat. Nos. 3,589,578 and 4,031,307, such as guar gums containing trialkylammonium cationic groups. Use can be made, for example, of guar gums modified with a salt (e.g. chloride) of 2,3-epoxypropyl-trimethylammonium.

Such products are sold for example, under the trade names Jaguar C13S, Jaguar C15, Jaguar C17 and Jaguar C162 by the company Meyhall.

(5) Polymers comprising piperazinyl units and divalent alkylene or hydroxyalkylene radicals containing straight or branched chains, optionally interrupted by oxygen, sulphur or nitrogen atoms or by aromatic or heterocyclic rings, and also the oxidation and/or quaternization products of these polymers. Such polymers are described, for example, in French Patent Nos. FR-2 162 025 and FR-2 280 361.

(6) Water-soluble polyaminoamides prepared, by polycondensation of an acidic compound with a polyamine; these polyaminoamides can be crosslinked with an epihalohydrin, a diepoxide, a dianhydride, an unsaturated dianhydride, a bisunsaturated derivative, a bishalohydrin, a bisazetidinium, a bishaloacyldiamine, a bisalkyl halide or alternatively with an oligomer resulting from the reaction of a difunctional compound which is reactive with a bishalohydrin, a bisazetidinium, a bishaloacyldiamine, a bisalkyl halide, an epihalohydrin, a diepoxide or a bisunsaturated derivative; the crosslinking agent being used in an amount ranging from 0.025 mol to 0.35 mol per amine group of the polyaminoamide; these polyaminoamides can be alkylated or, if they contain at least one tertiary amine functional groups, they can be quaternized. Such polymers are described, for instance, in French Patent Nos. FR-2 252 840 and FR-2 368 508.

(7) The polyaminoamide derivatives resulting from the condensation of polyalkylene polyamines with polycarboxylic acids followed by alkylation with difunctional agents. Non-limiting mention may be made, for example, of adipic acid/dialkylaminohydroxyalkyldialkylenetriamine polymers in which the alkyl radical contains from 1 to 4 carbon atoms, and can be, for example, methyl, ethyl or propyl. Such polymers are described for instance, in French Patent No. FR-1 583 363.

Among these derivatives, mention may be made for example, of the adipic acid/dimethylaminohydroxypropyl/diethylenetriamine polymers sold under the name "Cartaretine F, F4 or F8" by the company Sandoz.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid ranges from 0.8:1 to 1.4:1; the polyaminoamide resulting therefrom is reacted with epichlorohydrin in a molar ratio of epichlorohydrin relative to the secondary amine group of the polyaminoamide ranging from 0.5:1 to 1.8:1. Such polymers are described for instance in U.S. Pat. Nos. 3,227,615 and 2,961,347.

Polymers of this type are sold, for example, under the name "Hercosett 57" by the company Hercules Inc. or alternatively under the name "PD 170" or "Delsette 101" by the company Hercules in the case of the adipic acid/epoxypropyl/diethylenetriamine copolymer.

(9) Cyclopolymers of alkyldiallylamine or of dialkyldiallylammonium, such as the homopolymers or copolymers containing, as main constituent of the chain, units chosen from those of formulae (V) and (VI):

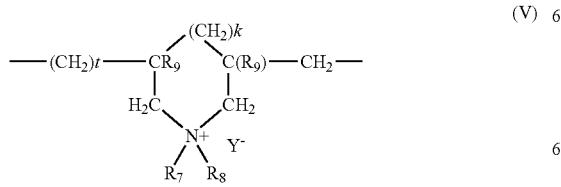

(V)

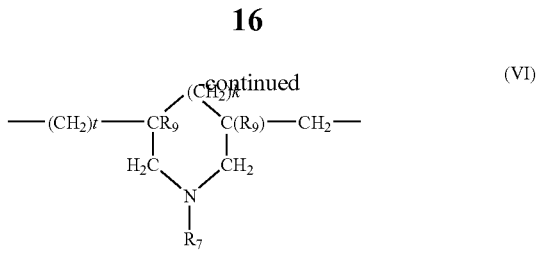

(VI)

in which formulae k and t are equal to 0 or 1, the sum k+t being equal to 1; $R_9$ is chosen from hydrogen atoms and methyl radicals; $R_7$ and $R_8$, independently of each other, are chosen from alkyl groups having from 1 to 6 carbon atoms, hydroxyalkyl groups in which the alkyl group has, for example, 1 to 5 carbon atoms, and lower ($C_1$-$C_4$) amidoalkyl groups, or, alternatively, $R_7$ and $R_8$ can, together with the nitrogen atom to which they are attached, form heterocyclic groups such as piperidyl or morpholinyl; $R_7$ and $R_8$, independently of each other, can be for instance, chosen from alkyl groups having from 1 to 4 carbon atoms; $Y^-$ is an anion such as bromide, chloride, acetate, borate, citrate, tartrate, bisulphate, bisulphite, sulphate or phosphate. These polymers are described, for example, in French Patent No. 2 080 759 and in its Certificate of Addition 2 190 406.

Among the polymers defined above, mention may be made for instance of the dimethyidiallylammonium chloride homopolymer sold under the name "Merquat 100" by the company Calgon (and its homologues of low weight-average molecular mass) and the copolymers of diallyldimethylammonium chloride and of acrylamide, sold under the name "Merquat 550."

(10) The quaternary diammonium polymer containing repeating units of formula (VII):

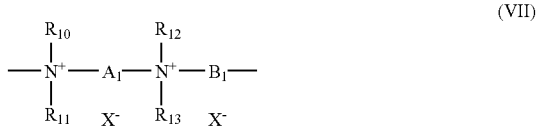

(VII)

in which formula (VII):

R10, R11, R12 and R13, which may be identical or different, are chosen from aliphatic, alicyclic and arylaliphatic radicals containing from 1 to 20 carbon atoms, and lower hydroxyalkylaliphatic radicals, or alternatively R10, R11, R12 and R13, together or separately, form, with the nitrogen atoms to which they are attached, heterocycles optionally containing a second heteroatom other than nitrogen, or alternatively R10, R11, R12 and R13 are chosen from linear and branched C1-C6 alkyl radicals substituted with a nitrile, ester, acyl or amide group or a group —CO—O—R14-D or —CO—NH—$R_{14}$-D where $R_{14}$ is an alkylene and D is a quaternary ammonium group;

$A_1$ and $B_1$ are polymethylene groups containing from 2 to 20 carbon atoms which may be linear or branched, saturated or unsaturated, and which may contain, linked to or intercalated in the main chain, at least one aromatic ring or at least one entity chosen from oxygen and sulphur atoms and sulphoxide, sulphone, disulphide, amino, alkylamino, hydroxyl, quaternary ammonium, ureido, amide and ester groups, and $X^-$ is an anion derived from an inorganic or organic acid;

$A_1$, $R_{10}$ and $R_{12}$ can form, with the two nitrogen atoms to which they are attached, a piperazine ring; in addition, if $A_1$ is a linear or branched, saturated or unsaturated alkylene or hydroxyalkylene radical, $B_1$ can also be a group $-(CH_2)_n-CO-D-OC-(CH_2)_n-$ in which D is chosen from:
a) a glycol residue of formula: $-O-Z-O-$, where Z is chosen from linear and branched hydrocarbon-based radicals and groups corresponding to the formulae:

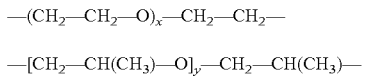

where x and y are integers ranging from 1 to 4, representing a defined and unique degree of polymerization, or any number from 1 to 4 representing an average degree of polymerization;
b) a bissecondary diamine, residue such as a piperazine derivative;
c) a bisprimary diamine residue of formula: $-NH-Y-NH-$, where Y is chosen from linear and branched hydrocarbon-based radicals, or alternatively the divalent radical

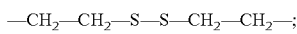

d) a ureylene group of formula: $-NH-CO-NH-$.

For example, $X^-$ can be an anion such as chloride or bromide.

These polymers generally have a number-average molecular mass ranging from 1,000 to 100,000.

Polymers of this type are described for instance, in French Patent Nos. FR-2 320 330, FR-2 270 846, FR-2 316 271, FR-2 336 434 and FR-2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is also possible, for example, to use polymers that comprise repeating units of formula (VIII):

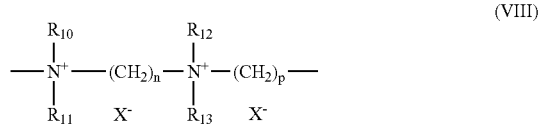

(VIII)

in which $R_{10}$, $R_{11}$, $R_{12}$ and $R_{13}$, which may be identical or different, are chosen from alkyl and hydroxyalkyl radicals containing from 1 to 4 carbon atoms approximately, n and p are integers ranging from 2 to 20 approximately, and $X^-$ is an anion derived from a mineral or organic acid.

(11) Polyquaternary ammonium polymers comprising repeating units of formula (IX):

in which p is an integer ranging from 1 to 6, D may be nothing or may be a group $-(CH_2)_r-CO-$ in which r is a number equal to 4 or 7, and $X^-$ is an anion.

Such polymers may be prepared according to the processes described in U.S. Pat. Nos. 4,157,388, 4,702,906 and 4,719,282. They are also described in European Patent Application No. EP-A-122 324.

Among these polymers, examples that may be mentioned include the products "Mirapol A 15," "Mirapol AD1", "Mirapol AZ1" and "Mirapol 175" sold by the company Miranol.

(12) Quaternary polymers of vinylpyrrolidone and of vinylimidazole, such as for instance the products sold under the names Luviquat FC 905, FC 550 and FC 370 by the company BASF.

(13) Polyamines such as Polyquart H sold by Henkel, which is given under the reference name "Polyethylene glycol (15) tallow polyamine" in the CTFA dictionary.

(14) Crosslinked methacryloyloxy($C_1$-$C_4$)alkyltri($C_1$-$C_4$) alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, for instance methylenebisacrylamide. A crosslinked acrylamide/methacryloyloxyethyltrimethylammonium chloride copolymer (20/80 by weight) in the form of a dispersion containing 50% by weight of the said copolymer in mineral oil can also be used, for example. This dispersion is sold under the name "Salcare® SC 92" by the company Allied Colloids. A crosslinked methacryloyloxyethyltrimethylammonium chloride homopolymer containing about 50% by weight of the homopolymer in mineral oil or in a liquid ester can also be used. These dispersions are sold under the names "Salcare® SC 95" and "Salcare® SC 96" by the company Allied Colloids.

(15) Other cationic polymers which can be used in the context of the disclosure are polyalkyleneimines, for instance polyethyleneimines, polymers containing vinylpyridine or vinylpyridinium units, condensates of polyamines and of epichlorohydrin, quaternary polyureylenes and chitin derivatives.

Among all the cationic polymers which may be used in the context of the present disclosure, in one embodiment the polymers are chosen from those of families (1), (9), (10), (11) and (14), and for example, the polymers containing repeating units of formulae (W) and (U) below:

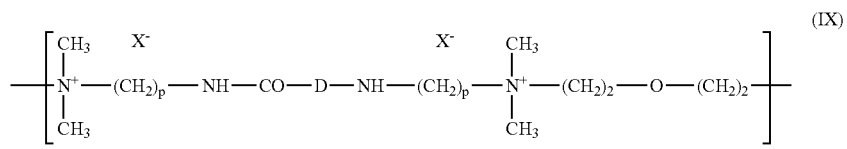

(IX)

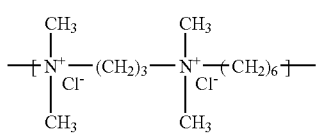 (W)

such as those whose molecular weight, determined by gel permeation chromatography, ranges from 9,500 to 9,900;

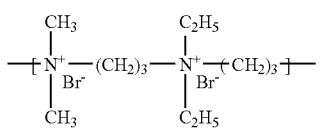 (U)

for instance, those whose molecular weight, determined by gel permeation chromatography, is about 1,200.

As regards the amphoteric polymer(s) that may be used in accordance with the present disclosure, they may be chosen from polymers comprising units K and M randomly distributed in the polymer chain, in which K is a unit derived from a monomer comprising at least one basic nitrogen atom and M is a unit derived from an acidic monomer comprising at least one group chosen from carboxylic and sulphonic groups, or alternatively K and M may be chosen from groups derived from zwitterionic carboxybetaine and sulphobetaine monomers;

K and M may also be chosen from cationic polymer chains comprising primary, secondary, tertiary or quaternary amine groups, in which at least one of the amine groups bears a carboxylic or sulphonic group linked via a hydrocarbon-based radical, or alternatively K and M form part of a chain of a polymer containing an α,β-dicarboxylic ethylene unit in which one of the carboxylic groups has been made to react with a polyamine comprising at least one group chosen from primary and secondary amine groups.

The amphoteric polymers corresponding to the above definition that may be mentioned include those chosen from the following polymers:

(1) Polymers resulting from the copolymerization of a monomer derived from a vinyl compound bearing a carboxylic group such as, for instance, acrylic acid, methacrylic acid, maleic acid, α-chloroacrylic acid, and from a basic monomer derived from a substituted vinyl compound containing at least one basic atom, such as, for instance, dialkylaminoalkyl methacrylate and acrylate, dialkylaminoalkyl-methacrylamide and -acrylamide. Such compounds are described in U.S. Pat. No. 3,836,537. Mention may also be made of the sodium acrylate/acrylamidopropyltrimethy-lammonium chloride copolymer sold under the name Polyquart KE 3033 by the company Henkel.

The vinyl compound may also be a dialkyldiallylammonium salt such as dimethyldiallylammonium chloride. The copolymers of acrylic acid and of the latter monomer are sold under the names Merquat 280, Merquat 295 and Merquat Plus 3330 by the company Calgon.

(2) Polymers containing units derived from:
  a) at least one monomer chosen from acrylamides and methacrylamides substituted on the nitrogen with an alkyl radical,
  b) at least one acidic comonomer containing at least one reactive carboxylic group, and
  c) at least one basic comonomer, such as esters containing primary, secondary, tertiary and quaternary amine substituents of acrylic and methacrylic acids and the product of quaternization of dimethylaminoethyl methacrylate with dimethyl or diethyl sulphate.

Among the N-substituted acrylamides or methacrylamides which may be used according to the disclosure are groups in which the alkyl radicals contain from 2 to 12 carbon atoms, such as N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen for example from acrylic acid, methacrylic acid, crotonic acid, itaconic acid, maleic acid and fumaric acid and alkyl monoesters, having 1 to 4 carbon atoms, of maleic or fumaric acids or anhydrides.

For example, the basic comonomers which may be used include aminoethyl, butylaminoethyl, N,N'-dimethylamino-ethyl and N-tert-butylaminoethyl methacrylates.

The copolymers whose CTFA (4th edition, 1991) name is Octylacrylamide/acrylates/butylaminoethyl methacrylate copolymer such as the products sold under the name Amphomer or Lovocryl 47 by the company National Starch may also be used.

(3) Polyaminoamides that are crosslinked and alkylated partially or totally derived from polyaminoamides of general formula:

 (X)

in which $R_{19}$ is chosen from divalent radicals derived from a saturated dicarboxylic acids, mono- and dicarboxylic aliphatic acids containing an ethylenic double bond, esters of a lower alkanol, having 1 to 6 carbon atoms, of these acids or a radical derived from the addition of any one of the acids to a bis(primary) or bis(secondary) amine, and Z is chosen from bis(primary), mono- and bis(secondary) polyalkylene-polyamine radicals, and for example, may be:
  a) in an amount ranging from 60 to 100 mol %, the radical

 (XI)

where x=2 and p=2 or 3, or alternatively x=3 and p=2 this radical being derived from diethylenetriamine, from triethylenetetraamine or from dipropylenetriamine;
  b) in an amount ranging from 0 to 40 mol %, the radical (XI) above in which x=2 and p=1 and which is derived from ethylenediamine, or the radical derived from piperazine:

c) in an amount ranging from 0 to 20 mol %, the —NH—$(CH_2)_6$—NH— radical derived from hexamethylenediamine, these polyaminoamines being crosslinked by addition of a difunctional crosslinking agent chosen from epihalohydrins, diepoxides, dianhydrides and bisunsaturated derivatives, using from 0.025 to 0.35 mol of crosslinking agent per amine group of the polyaminoamide and alkylated by the action of acrylic acid, chloroacetic acid or an alkane sultone, or salts thereof.

The saturated carboxylic acids can be chosen from, for example, acids having 6 to 10 carbon atoms, such as adipic acid, 2,2,4-trimethyladipic acid and 2,4,4-trimethyladipic acid, terephthalic acid and acids containing an ethylenic double bond, for instance acrylic acid, methacrylic acid and itaconic acid.

The alkane sultones used in the alkylation can be, for example, propane sultone or butane sultone, and the salts of the alkylating agents may be the sodium or potassium salts.

(4) Polymers containing zwitterionic units of formula:

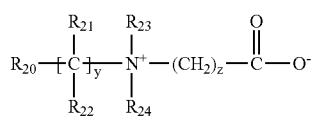
(XII)

in which $R_{20}$ is a polymerizable unsaturated group such as an acrylate, methacrylate, acrylamide or methacrylamide group, y and z are integers ranging from 1 to 3, $R_{21}$ and $R_{22}$ are chosen from hydrogen atoms, and methyl, ethyl and propyl groups, $R_{23}$ and $R_{24}$ are chosen from hydrogen atoms and alkyl radicals such that the sum of the carbon atoms in $R_{23}$ and $R_{24}$ does not exceed 10.

The polymers comprising such units can also contain units derived from non-zwitterionic monomers such as dimethyl or diethylaminoethyl acrylate or methacrylate or alkyl acrylates or methacrylates, acrylamides or methacrylamides or vinyl acetate.

By way of example, mention may be made of the copolymer of methyl methacrylate/methyl dimethylcarboxymethylammonioethyl methacrylate such as the product sold under the name Diaformer Z301 by the company Sandoz.

(5) Chitosan-based polymers comprising monomer units of formulae (XIII), (XIV) and (XV):

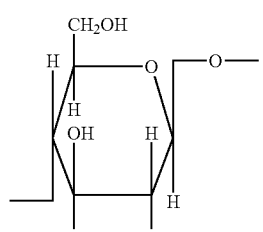
(XIII)

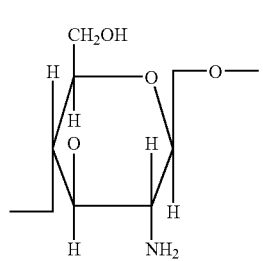
(XIV)

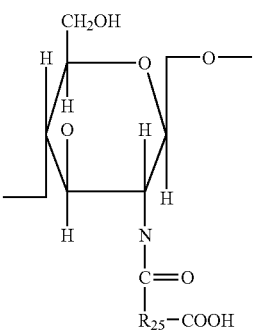
(XV)

the unit (XIII) being present in an amount ranging from 0 to 30%, the unit (XIV) in an amount ranging from 5% to 50%, and the unit (XV) in an amount ranging from 30% to 90%, it being understood that, in the unit (XV), $R_{25}$ is a radical of formula:

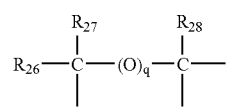

in which if q=0, $R_{26}$, $R_{27}$ and $R_{28}$, which may be identical or different, are chosen from hydrogen atoms, and methyl, hydroxyl, acetoxy and amino residues, monoalkylamine residues and dialkylamine residues which are optionally interrupted by at least one nitrogen atom and/or optionally substituted with at least one group chosen from amine, hydroxyl, carboxyl, alkylthio and sulphonic groups, alkylthio residues, in which the alkyl group bears an amino residue, at least one of the radicals $R_{26}$, $R_{27}$ and $R_{28}$ being, in this case, a hydrogen atom; of, if q=1, $R_{26}$, $R_{27}$ and $R_{26}$ are each a hydrogen atom, and also the salts formed by these compounds with bases or acids.

(6) Polymers derived from the N-carboxyalkylation of chitosan, such as N-carboxymethylchitosan or N-carboxybutylchitosan sold under the name "Evalsan" by the company Jan Dekker.

(7) Polymers of the general formula (XVI) such as those described, for example, in French Patent No. 1 400 366:

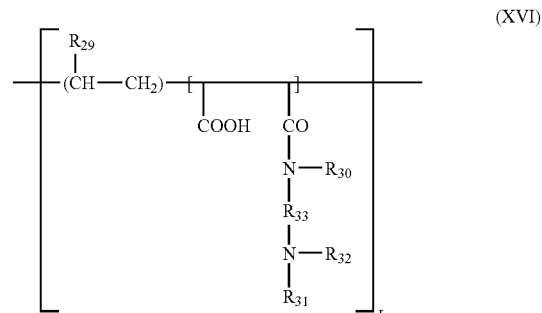
(XVI)

in which r is any number greater than 1; $R_{29}$ is chosen from a hydrogen atom, $CH_3O$, $CH_3CH_2O$ and phenyl radicals, $R_{30}$ is chosen from a hydrogen atom and lower alkyl radicals such as methyl or ethyl, $R_{31}$ is chosen from a hydrogen atom and lower alkyl radicals such as methyl or ethyl, $R_{32}$ is chosen from lower alkyl radicals such as methyl or ethyl, and radicals of the formula: —$R_{33}$—$N(R_{31})_2$, $R_{33}$ being chosen from —$CH_2$—$CH_2$—, —$CH_2$—$CH_2$—$CH_2$— and —$CH_2$—$CH(CH_3)$— groups, and $R_{31}$ having the meanings mentioned above, and also the higher homologues of these radicals and containing up to 6 carbon atoms.

(8) Amphoteric polymers of the type -D-X-D-X- chosen from:

a) polymers obtained by the action of chloroacetic acid or sodium chloroacetate on compounds containing at least one unit of formula:

-D-X-D-X-D-                              (XVII)

where D is the radical

and X is the symbol E or E', wherein E or E', which may be identical or different, are divalent radicals which can be an alkylene radical with a straight or branched chain containing up to 7 carbon atoms in the main chain, which is unsubstituted or substituted with hydroxyl groups and which can contain, in addition to the oxygen, nitrogen and sulphur atoms, 1 to 3 aromatic and/or heterocyclic rings; the oxygen, nitrogen and sulphur atoms being present in the form of ether, thioether, sulphoxide, sulphone, sulphonium, alkylamine or alkenylamine groups, hydroxyl, benzylamine, amine oxide, quaternary ammonium, amide, imide, alcohol, ester and/or urethane groups;

b) polymers of formula:

-D-X-D-X-                                (XVIII)

where D is the radical

and X is the symbol E or E" and at least once E"; E having the meaning given above and E" being a divalent radical which is an alkylene radical with a straight or branched chain having up to 7 carbon atoms in the main chain, which is unsubstituted or substituted with at least one hydroxyl radical and containing at least one nitrogen atom, the nitrogen atom being substituted with an alkyl chain which is optionally interrupted with an oxygen atom, and necessarily containing at least one group chosen from carboxyl and hydroxyl functional group and betainized by reaction with chloroacetic acid or sodium chloroacetate.

(9) $(C_1-C_5)$alkyl vinyl ether/maleic anhydride copolymers partially modified by semi-amidation with an N,N-dialkylaminoalkylamine such as N,N-dimethylaminopropylamine or by semi-esterification with an N,N-dialkanolamine. These copolymers can also contain other vinyl comonomers such as vinylcaprolactam.

In one embodiment, the amphoteric polymers according to the disclosure are those of family (1).

According to the disclosure, the cationic or amphoteric substantive polymer(s), when they are present, can be present in an amount ranging from 0.01% to 10% by weight, relative to the weight of the dye composition, for instance from 0.05% to 5% by weight, relative to the weight of the dye composition, such as from 0.1% to 3% by weight, relative to the weight of the dye composition.

The medium that is suitable for dyeing keratin fibers can consist of water or can comprises a mixture of water and at least one organic solvent to dissolve the compounds that are not sufficiently water-soluble. Examples of organic solvents that may be mentioned include $C_1$-$C_4$ lower alkanols, such as ethanol and isopropanol; polyols and polyol ethers, for instance 2-butoxyethanol, propylene glycol, propylene glycol monomethyl ether, diethylene glycol monoethyl ether and monomethyl ether, and also aromatic alcohols, for instance benzyl alcohol or phenoxyethanol, and mixtures thereof.

The solvents may be present in an amount ranging from 1% to 40% by weight, relative to the weight of the dye composition, such as from 5% to 30% by weight, relative to the weight of the dye composition.

The composition may also comprise at least one adjuvant common in the field, such as, for instance, organic or mineral thickeners; antioxidants; penetrants; sequestrants; fragrances; buffers; dispersants; conditioning agents other than the cationic or amphoteric substantive polymers, for instance cations, or volatile or non-volatile, modified or unmodified silicones; film-forming agents; ceramides; preserving agents; stabilizers; opacifiers.

Needless to say, a person skilled in the art will take care to select this or these optional additional compound(s) such that the beneficial properties intrinsically associated with the composition in accordance with the disclosure are not, or are not substantially, adversely affected by the envisaged addition(s).

As indicated previously, the present disclosure also relates to a process for dyeing keratin materials using the composition according to the disclosure.

According to one embodiment, the process comprises applying the composition, in the absence of an oxidizing agent, to keratin materials, for example wet or dry fibers, with or without final rinsing of the composition. In the case of this embodiment, the composition according to the disclosure does not comprise any oxidation dye precursor, but at least one direct dyes.

According to another embodiment of the disclosure, the process comprises applying the composition according to the disclosure, in the presence of at least one oxidizing agent, to wet or dry keratin materials, and then leaving it on for a period of time that is sufficient to obtain the desired coloration.

According to another embodiment, at least one dye composition according to the disclosure and at least one oxidizing composition are applied to the keratin fibers simultaneously or successively without intermediate rinsing.

As disclosed herein, the composition applied is considered a "ready-to-use composition," when the composition is obtained by extemporaneous mixing of at least one dye composition according to the disclosure with a composition comprising at least one oxidizing agent.

In this case, the dye composition may comprise at least one oxidation dye precursor. It may also comprise at least one direct dye, when lightening of the keratin fibers is desired in combination with dyeing.

As disclosed herein, the dye composition may comprise a combination of oxidation dye precursors and of direct dyes.

The at least one oxidizing agent present in the oxidizing composition may be chosen, for example, from hydrogen peroxide, urea peroxide, alkali metal bromates, persalts such as perborates and persulphates, and enzymes such as peroxidases and two-electron or four-electron oxidoreductases. In one embodiment of the disclosure, hydrogen peroxide is used.

The at least one oxidizing agent can be present in an amount ranging from 1% to 40% by weight, relative to the weight of the ready-to-use composition, such as from 1% to 20% by weight, relative to the weight of the ready-to-use composition.

As disclosed herein, the oxidizing composition used can be aqueous composition and may be in the form of a solution or an emulsion.

In one embodiment, the composition free of oxidizing agent is mixed with about 0.5 to 10 weight equivalents of the oxidizing composition.

It should be noted that the pH of the ready-to-use composition can range from 3 to 12, for instance from 4 to 11, such as from 6.5 to 10.5.

The pH of the ready-to-use composition may be adjusted using a basifying or acidifying agent chosen for example, from those mentioned previously.

Still in the case where the composition is applied in the presence of at least one oxidizing agent, the process may comprise a preliminary step that comprises separately storing, in at least one first compartment, at least one dye composition according to the disclosure and, in at least one second compartment, at least one composition comprising at least one oxidizing agent in a medium that is suitable for dyeing human keratin fibers, and then in mixing them together at the time of use, before applying this mixture to the wet or dry keratin materials.

Irrespective of whether the process is performed in the presence or absence of at least one oxidizing agent, the time required to develop the coloration can range from a few seconds to 60 minutes, such as from 1 to 50 minutes.

The temperature required to develop the coloration can range from room temperature (15 to 25° C.) to 250° C., for instance from room temperature to 180° C., such as from room temperature to 60° C.

Once the time required to develop the coloration has elapsed, the composition is may be removed.

This may take place in a conventional manner, either by performing at least one rinsing operation, or by performing at least one washing and rinsing operations, or any combination thereof. Finally, the keratin materials can be dried or are left to dry.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in its respective testing measurement.

The examples that follow are intended to illustrate the disclosure without, however, being limiting in nature.

EXAMPLES

The following dye compositions of the disclosure were prepared (the amounts are expressed in grams):

|  | A | B | C |
|---|---|---|---|
| Double-distilled pure cetyl alcohol (Lanette 16; from Cognis) | 10.2 | 10.2 | 10.2 |
| Polyglycerolated (2 mol) oleyl alcohol | 4 | 4 | — |
| Oxyethylenated (10 EO) oleyl alcohol (Brij 96 V; from Uniquema) | — | — | 4 |
| Glyceryl stearate (Tegin 6070; from Goldschmidt) | 5.8 | 5.8 | 5.8 |
| Cetyl oleate (Cetiol V; from Cognis) | 1.8 | 1.8 | — |
| Glycol distearate (Tegin BL 315; from Goldschmidt) | — | — | 1.8 |
| Sodium laurylpolyglucoside (n = 1.4) ether carboxylate at 30% in water (Plantapon LGC SORB; from Cognis) | 0.8 | — | — |
| Oleic acid | 2.73 | 2.73 | 2.73 |
| Pure monoethanolamine | 0.52 | 0.52 | 0.52 |
| PEG-18/5-dodoxynol/PEG-25 tristyrylphenol/tetramethoxymethylglycolurile copolymer (Pure Thix TX-1442; from Süd Chemie) | — | — | 0.1 |
| PEG-180/laureth-50/TMMG copolymer (Pure Thix TX-1450; from Süd Chemie) | — | 0.1 | — |
| Polymer SMDI/decyl-terminated polyethylene glycol in aqueous glycolic solution (PEG-150/decyl alcohol/SMDI copolymer; Aculyn 44; from Rohm & Haas) | 0.4 | — | — |
| Nonstabilized polydimethyldiallylammonium chloride in water at 40% (polyquaternium-6) | — | — | 2 |
| Sodium metabisulphite | — | — | 0.71 |
| Ammonium thiolactate in aqueous solution at 58% | 0.8 | 0.8 | — |
| Ascorbic acid | 0.25 | 0.25 | 0.25 |
| Titanium oxide (untreated anatase) coated with polydimethylsiloxane (98/2) | 0.15 | 0.15 | 0.15 |
| Citric acid | 0.31 | 0.31 | 0.31 |
| Aqueous ammonia (20% ammonia) | 11.1 | 11.1 | 11.1 |
| 1-hydroxy-4-aminobenzene | 0.545 | 0.545 | 0.545 |
| 1-methyl-2-hydroxy-4-aminobenzene | 0.615 | 0.615 | 0.615 |
| Fragrance | 0.95 | 0.95 | 0.95 |
| Deionized water | 59.03 | 60.13 | 58.22 |

The above dye compositions were mixed, at the time of use, in a plastic bowl and for 2 minutes, with an aqueous oxidizing composition containing 6% aqueous hydrogen peroxide solution, at a rate of 1 part of dye composition per 1.5 parts of oxidizing composition. The mixing was quick and easy.

The mixtures obtained were applied to locks of natural hair containing 90% white hairs and were left on for 20 minutes. The applications were quick and easy. The product stayed in place perfectly, does not run, and spread well from the root to the end.

The locks were then rinsed with water, washed with a standard shampoo, rinsed again with water, and then dried and disentangled. The mixtures were satisfactorily removed on rinsing.

The hair was dyed in a strong coppery red shade. Furthermore, the hair was not coarse.

What is claimed is:

1. A dye composition comprising, in a medium suitable for dyeing keratin fibers:
    at least one dye chosen from oxidation dye precursors and direct dyes;
    at least one fatty alcohol;

at least one fatty acid ester of a $C_1$-$C_{10}$ alcohol wherein the at least one fatty acid ester is chosen from a monoesters of linear and branched, saturated and unsaturated $C_8$-$C_{30}$ carboxylic acids and of linear and branched, saturated and unsaturated $C_1$-$C_{10}$ monohydroxylated alcohols;

at least one surfactant chosen from non-ionic surfactants and anionic surfactants; and at least one non-ionic associative polymer; wherein water is present in an amount greater than or equal to 55% by weight, relative to the weight of the dye composition.

2. The dye composition according to claim 1, wherein water is present in an amount of greater than or equal to 60% by weight, relative to the weight of the dye composition.

3. The dye composition according to claim , wherein the at least one fatty alcohol is present in an amount ranging from 0.1% to 30% by weight, relative to the weight of the dye composition.

4. The dye composition according to claim 1, wherein the at least one fatty acid ester of a $C_1$-$C_{10}$ alcohol is chosen from monoesters of oleic acid, lauric acid, palmitic acid, myristic acid, behenic acid, stearic acid, linoleic acid, linolenic acid, capric acid or arachidonic acid, and of methanol, ethanol, propanol, isopropanol, ethylene glycol, glycerol, octanol, and decanol.

5. The dye composition according to claim 1, wherein the at least one fatty acid ester of a $C_1$-$C_{10}$ alcohol is present in an amount ranging from 0.1% to 30% by weight, relative to the weight of the dye composition.

6. The dye composition according to claim 1, wherein the at least one non-ionic surfactant is chosen from:
   oxyalkylenated and glycerolated fatty alcohols;
   oxyalkylenated alkylphenols in which the alkyl chain is of $C_8$-$C_{18}$;
   oxyalkylenated and glycerolated fatty amides;
   oxyalkylenated plant oils;
   optionally oxyalkylenated fatty acid esters of sorbitan;
   optionally oxyalkylenated fatty acid esters of sucrose;
   fatty acid esters of polyethylene glycol;
   ($C_6$-$C_{30}$)alkyl polyglycosides;
   N-($C_6$-$C_{30}$)alkylglucamine derivatives;
   amine oxides; and
   copolymers of ethylene oxide and of propylene oxide.

7. The dye composition according to claim 6, wherein the at least one non-ionic surfactant is chosen from ($C_{10}$-$C_{14}$) alkylamine oxides and N-acylaminopropylmorpholine oxides.

8. The dye composition according to claim 1, wherein the at least one anionic surfactant is chosen from:
   ($C_6$-$C_3$)alkyl sulphates, ($C_6$-$C_3$)alkyl ether sulphates, ($C_6$-$C_{30}$)alkylamido ether sulphates, alkylaryl polyether sulphates, monoglyceride sulphates;
   ($C_6$-$C_3$)alkyl sulphonates, ($C_6$-$C_{30}$)alkylamide sulphonates, ($C_6$-$C_{30}$)alkylaryl sulphonates, α-olefin sulphonates, paraffin sulphonates;
   ($C_6$-$C_{30}$)alkyl phosphates;
   ($C_6$-$C_{30}$)alkyl sulphosuccinates, ($C_6$-$C_{30}$)alkyl ether sulphosuccinates, ($C_6$-$C_{30}$)alkylamide sulphosuccinates;
   ($C_6$-$C_3$)alkyl sulphoacetates;
   ($C_6$-$C_{24}$)acyl sarcosinates;
   ($C_6$-$C_{24}$)acyl glutamates;
   ($C_6$-$C_{30}$)alkylpolyglycoside carboxylic ethers; ($C_6$-$C_{30}$) alkylpolyglycoside sulphosuccinates;
   ($C_6$-$C_{30}$)alkyl sulphosuccinamates;
   ($C_6$-$C_{24}$)acyl isethionates;
   N-($C_6$-$C_{24}$)acyl taurates;
   $C_6$-$C_{30}$ fatty acid salts;
   ($C_8$-$C_{20}$)acyl lactylates;
   ($C_6$-$C_{30}$)alkyl-D-galactoside uronic acid salts;
   polyoxyalkylenated ($C_6$-$C_{30}$)alkyl ether carboxylic acid salts, polyoxyalkylenated ($C_6$-$C_{30}$)alkylaryl ether carboxylic acid salts, and polyoxyalkylenated ($C_6$-$C_{30}$) alkylamido ether carboxylic acid salts.

9. The dye composition according to claim 1, wherein the at least one surfactant chosen from non-ionic surfactants and anionic surfactants are present in a total amount ranging from 0.1% to 40% by weight, relative to the weight of the dye composition.

10. The dye composition according to claim 1, further comprising at least one fatty substance other than the fatty alcohol.

11. The dye composition according to claim 10, wherein the at least one fatty substance is chosen from non-oxyalkylenated, non-glycerolated fatty acid amides; carboxylic acid monoesters and polyesters; mineral oils and plant oils.

12. The dye composition according to claim 1, wherein the at least one non-ionic associative polymer is chosen from:
   (1) celluloses modified with groups comprising at least one fatty chain;
   (2) hydroxypropyl guars modified with groups comprising at least one fatty chain;
   (3) copolymers of vinylpyrrolidone and of hydrophobic monomers comprising a fatty chain;
   (4) copolymers of $C_1$-$C_6$ alkyl methacrylates or acrylates and of amphiphilic monomers comprising at least one fatty chain;
   (5) copolymers of hydrophilic methacrylates or acrylates and of hydrophobic monomers comprising at least one fatty chain;
   (6) polyether polyurethanes comprising, in their chain, hydrophilic blocks that are most commonly polyoxyethylenated in nature, and hydrophobic blocks which may be aliphatic chains alone and/or cycloaliphatic and/or aromatic chains; and
   (7) polymers with an aminoplast-ether backbone having at least one fatty chain.

13. The dye composition according to claim 1, wherein the at least one non-ionic associative polymer is present in an amount ranging from 0.01% to 5% by weight, relative to the weight of the dye composition.

14. The dye composition according to claim 1, wherein the at least one oxidation dye precursor is chosen from oxidation bases and couplers.

15. The dye composition according to claim 14, wherein the at least one oxidation dye precursor is an oxidation base, which is present in an amount ranging from 0.0005% to 12% by weight, relative to the weight of the dye composition.

16. The dye composition according to claim 14, wherein the at least one oxidation dye precursor is a coupler, which is present in an amount ranging from 0.0001% to 15% by weight, relative to the weight of the dye composition.

17. The dye composition according to claim 1, wherein the at least one direct dye is present in an amount ranging from 0.0005% to 15% by weight, relative to the weight of the dye composition.

18. The dye composition according to claim 1, further comprising at least one basifying agent.

19. The dye composition according to claim 18, wherein the at least one basifying agent is chosen from aqueous ammonia, alkanolamines and combinations of $C_2$-$C_{10}$ alkanolamines with alkali metal or alkaline-earth metal silicates.

20. The dye composition according to claim 1, further comprising at least one substantive polymer chosen from cationic and amphoteric substantive polymers.

21. The dye composition according to claim 20, wherein the at least one substantive polymer chosen from cationic and amphoteric substantive polymers is present in an amount ranging from 0.01% to 10% by weight, relative to the weight of the dye composition.

22. The dye composition according to claim 1, further comprising at least one oxidizing agent.

23. A process for dyeing keratin fibers, comprising applying a dye composition to said fibers, which may be dry or wet,
   wherein the dye composition comprises, in a medium suitable for dyeing keratin fibers:
   at least one dye chosen from oxidation dye precursors and direct dyes;
   at least one fatty alcohol; at least one fatty acid ester of a $C_1$-$C_{10}$ alcohol, wherein the at least one fatty acid ester is chosen from a monoesters of linear and branched, saturated and unsaturated $C_8$-$C_{30}$ carboxylic acids and of linear and branched, saturated and unsaturated $C_1$-$C_{10}$ monohydroxylated alcohols;
   at least one surfactant chosen from non-ionic surfactants and anionic surfactants; and
   at least one non-ionic associative polymer;
   wherein water is present in an amount greater than or equal to 55% by weight, relative to the weight of the dye composition.

24. A process for dyeing keratin fibers, comprising applying a dye composition to said fibers, which may be dry or wet, in the presence of an oxidizing composition comprising at least one oxidizing agent, which is applied simultaneously with or successively to the dye composition without intermediate rinsing, the mixture is left on the fibers, and the fibers are rinsed,
   wherein the dye composition comprises, in a medium suitable for dyeing keratin fibers:
   at least one dye chosen from oxidation dye precursors and direct dyes; at least one fatty alcohol;
   at least one fatty acid ester of a $C_1$-$C_{10}$ alcohol, wherein the at least one fatty acid ester is chosen from a monoesters of linear and branched, saturated and unsaturated $C_8$-$C_{30}$ carboxy lic acids and of linear and branched saturated and unsaturated $C_1$-$C_{10}$ monohydroxylated alcohols;
   at least one surfactant chosen from non-ionic surfactants and anionic surfactants; and
   at least one non-ionic associative polymer;
   wherein water is present in an amount greater than or equal to 55% by weight, relative to the weight of the dye composition.

25. A process for dyeing keratin fibers, comprising applying a dye composition to said fibers, which may be dry or wet, in the presence of an oxidizing composition comprising at least one oxidizing agent, which is mixed with the dye composition before application, the mixture is left on the fibers, and the fibers are rinsed,
   wherein the dye composition comprises, in a medium suitable for dyeing keratin fibers:
   at least one dye chosen from oxidation dye precursors and direct dyes;
   at least one fatty alcohol;
   at least one fatty acid ester of a $C_1$-$C_{10}$ alcohol, wherein the at least one fatty acid ester is chosen from a monoesters of linear and branched, saturated and unsaturated $C_8$-$C_{30}$ carboxylic acids and of linear and branched, saturated and unsaturated $C_1$-$C_{10}$ monohvd roxylated alcohols;
   at least one surfactant chosen from non-ionic surfactants and anionic surfactants; and
   at least one non-ionic associative polymer;
   wherein water is present in an amount greater than or equal to 55% by weight, relative to the weight of the dye composition.

26. A multi-compartment kit for dyeing keratin fibers, comprising
   at least one first compartment containing a dye composition comprising, in a medium suitable for dyeing keratin fibers:
   at least one dye chosen from oxidation dye precursors and direct dyes;
   at least one fatty alcohol;
   at least one fatty acid ester of a $C_1$-$C_{10}$ alcohol, wherein the at least one fatty acid ester is chosen from a monoesters of linear and branched, saturated and unsaturated $C_8$-$C_{30}$ carboxylic acids and of linear and branched, saturated and unsaturated $C_1$-$C_{10}$ monohydroxylated alcohols;
   at least one surfactant chosen from non-ionic surfactants and anionic surfactants; and
   at least one non-ionic associative polymer;
   wherein water is present in an amount greater than or equal to 55% by weight, relative to the weight of the dye composition; and
   at least one second compartment containing an oxidizing composition comprising at least one oxidizing agent.

* * * * *

UNITED STATES PATENT AND TRADEMARK OFFICE
CERTIFICATE OF CORRECTION

PATENT NO. : 7,442,214 B2
APPLICATION NO. : 11/393696
DATED : October 28, 2008
INVENTOR(S) : Frédéric Legrand It is certified that error appears in the above-identified patent and that said Letters Patent is hereby corrected as shown below:

In claim 3, column 27, line 14, "claim ," should read --claim 1,--.

In claim 8, column 27, line 49, "$(C_6-C_3)$alkyl sulphates," should read --$(C_6-C_{30})$alkyl sulphates,--.

In claim 8, column 27, line 49, "$(C_6-C_3)$alkyl ether" should read --$(C_6-C_{30})$alkyl ether--.

In claim 8, column 27, line 52, "$(C_6-C_3)$alkyl" should read --$(C_6-C_{30})$alkyl--.

In claim 8, column 27, line 58, "$(C_6-C_3)$alkyl" should read "$(C_6-C_{30})$alkyl--.

In claim 24, column 29, line 40, "carboxy lic" should read --carboxylic--.

In claim 25, column 30, line 16, "$C_1-C_{10}$ monohvd roxylated" should read --$C_1-C_{10}$ monohydroxylated--.

Signed and Sealed this

Seventeenth Day of February, 2009

JOHN DOLL
*Acting Director of the United States Patent and Trademark Office*